United States Patent [19]

Takasaki

[11] Patent Number: 4,657,865

[45] Date of Patent: Apr. 14, 1987

[54] PULLULANASE-LIKE ENZYME, METHOD FOR PREPARATION THEREOF, AND METHOD FOR SACCHARIFICATION OF STARCH THEREWITH

[75] Inventor: Yoshiyuki Takasaki, Matsudo, Japan

[73] Assignees: Agency of Industrial Science & Technology; Ministry of International Trade & Industry, both of Tokyo, Japan

[21] Appl. No.: 719,244

[22] Filed: Apr. 2, 1985

[30] Foreign Application Priority Data

Jan. 7, 1985 [JP] Japan .................................... 60-588

[51] Int. Cl.$^4$ ..................... C12N 9/28; C12N 9/44; C12P 19/16; C12P 19/14; C12R 1/125

[52] U.S. Cl. ..................... 435/202; 435/98; 435/99; 435/210; 435/839

[58] Field of Search ................... 435/98, 99, 96, 210, 435/202

[56] References Cited

U.S. PATENT DOCUMENTS

| | | | |
|---|---|---|---|
| 4,251,630 | 2/1981 | Pratt et al. ........................... | 435/98 |
| 4,318,989 | 3/1982 | Marshall .............................. | 435/210 |
| 4,355,110 | 10/1982 | Line et al. ........................... | 435/210 |
| 4,469,791 | 9/1984 | Colson et al. ....................... | 435/253 |

OTHER PUBLICATIONS

Takasaki, Agr. Biol Chem. 40(8), 1523–1530 (1976).

*Primary Examiner*—Lionel M. Shapiro
*Attorney, Agent, or Firm*—Oblon, Fisher, Spivak, McClelland & Maier

[57] ABSTRACT

A method for the production of a pullulanase-like enzyme possessing an α-amylase activity from a strain of genus *Bacillus subtilis,* the produced enzyme being capable of acting on starch to enhance the yield of glucose.

3 Claims, 2 Drawing Figures

4,657,865

PULLULANASE-LIKE ENZYME, METHOD FOR PREPARATION THEREOF, AND METHOD FOR SACCHARIFICATION OF STARCH THEREWITH

BACKGROUND OF THE INVENTION

1. Field of the Invention

This invention relates to a pullulanase-like enzyme, a method for the preparation thereof, and a method for the saccharification of starch with the enzyme.

2. Description of the Prior Art

Pullulanase is an enzyme which cleaves the α-1,6-glucosidic linkages of pullulan and eventually produces maltotriose. It is known to be produced by various bacteria and streptomyces. It is known that the pullulanase, when left acting upon amylopectin or starch containing amylopectin, cleaves the branched linkages (α-1,6-glucosidic linkages) thereof and gives rise to an amylose-like polysaccharide and, therefore, causes increase of the iodine reaction. It is, however, incapable of cleaving the α-1,4-glucosidic linkages. In contrast, amylases such as α-amylase and β-amylase which cleave the α-1,4-glucosidic linkages are incapable of cleaving the α-1,6-glucosidic linkages. As a very rare exception, glucomaylase is capable of cleaving not only the α-1,4-glucosidic linkages but also the α-1,6-glucosidic linkages.

In the enzymes which cleave the α-1,6-glucosidic linkages, there are included, besides pullulanase, various enzymes called isoamylase, R-enzyme, and amylo-1,6-glucosidase. These enzymes are collectively referred to as α-1,6-glucosidases or, more commonly, as debranching enzymes.

Recently, these debranching enzymes including pullulanase are used in conjunction with β-amylases to product maltose from starch in high yields through their cooperation on the starch. With a view to making upon for glucoamylases' insufficient ability to cleave branches (α-1,6-glucosidic linkages), they are also used in conjunction with such glucoamylases so as to permit production of glucose from starch in high yields. Thus, the debranching enzymes are useful even for the production of glucose.

For pullulanase to be effectively used jointly with glucoamylase, for instance, since glucoamylase optimally works in a pH range of 4 to 5 and a temperature range of 55° to 60° C., the pullulanase has to possess normal thermal stability to withstand the temperatures of 55° to 60° C. for a long time and work effectively at pH 4 to 5.

Unfortunately, numerous debranching enzymes heretofore known to the art, with the exception of a few of microorganic origins (Bacillus stearothermophilus (Collection of Summaries of Lectures for the 1972 Annual Meeting of Japan Agriculture Chemical Society, page 88, optimum temperature 65° to 67.5° C.) and Bacillus acidopulluliticus (Japanese Patent Public Disclosure SHO 57(1982)-174089; Starch 34, 340 (1982), optimum temperature 60° C.)), have their optimum temperatures in the neighborhood of 40° to 50° C., thus suffering from inferior thermal stability.

An object of this invention is to provide a thermostable pullulanase-like enzyme possessing the optimum pH in the range of about 5 to about 7.5.

Another object of this invention is to provide the enzyme capable of producing maltose and maltotriose in high yields.

A further object of this invention is to provide a method for promoting the saccharification of starch by glucoamylase and therefore enhancing the yield of glucose.

SUMMARY OF THE INVENTION

This invention is directed to effecting hydrolysis of starch by the use of a pullulanase-like enzyme possessing α-amylase activity, which enzyme is formed by culturing a strain of genus Bacillus capable of producing the aforementioned enzyme.

Since the aforementioned enzyme has a wide working pH range of 5 to 7.5, it is enabled to act upon starch in conjuntion with glucoamylase and consequently improve the yield of glucose. Besides possessing an ability to cleave the α-1,6-glucosidic linkages, this enzyme has an ability to cleave the α-1,4-glucosidic linkages and produce maltose and maltotriose from starch. The enzyme, when left acting on starch, can derive a sugar solution containing maltose and maltotriose in high concentrations.

The other objects and characteristic features of the present invention will become more apparent from the description given in detail below with reference to the accompanying drawings.

DESCRIPTION OF PREFERRED EMBODIMENT

The inventor has screened a host of microorganisms occuring widely in nature with a view to developing a debranching enzyme which fulfills the objects described above and has found that a thermostable pullulanase-like enzyme possessing a wide optimum pH range of about 5 to about 7.5 is provided by a bacterium identified to be *Bacillus subtilis*.

This enzyme, when allowed to act upon pullulan, exhibits an α-1,6-glucosidase activity high enough to hydrolyze pullulan substantially into maltotriose. When the same enzyme is allowed to act on starch, it exhibits a novel, interesting enzymatic activity to produce maltose and maltotriose specifically in high yields. It has been ascertained by the inventor that this enzyme permits production of novel starch syrup containing maltose and maltotriose each in a concentration of about 40 to 50% from starch. This invention has been perfected on the basis of this knowledge.

The aforementioned pullulanase-like enzyme possessing the α-amylase activity, when pullulan is used as the substrate, exhibits a pullulanase activity for eventually forming chiefly maltotriose. It also possesses an activity to cleave the α-1,4-glucosidic linkages such as of amylopectin and glycogen and form chiefly maltose and maltotriose. The pullulanase activity and the α-amylase activity of the enzyme are not separated by such protein-refining methods as ammonium sulfate fractionation, fractionation with various organic solvents, adsorption chromatography with an anion-exchanger, gel filtration, and adsorption on an inorganic carrier. The molecular weight of this enzyme, determined by the method of gel filtration using Sephadex G-200 (produced by Pharmatia Fine Chemicals), Cellulofine GC-700 m (produced by Chisso Corporation), or Biogel A-0.5 m (produced by Bio-Rad Lab.) was found to be 450,000 to 550,000 (cf. the molecular weight of an ordinary pullulanase which is about 100,000). Thus, it is proper to infer that a plurality of subunits possessing the aforementioned activities are bound quite strongly to form a composite enzyme. (FIG. 3, which shows the elution patterns of α-amylase activity (curve "b"), pullulanase activity (curve "a"), and proteins (curve "c") by Biogel A-1.5 m, clearly indicates agreement in the three elution patterns.)

The enzymatic properties of the pullulanase activity of the enzyme of this invention will be described below.

(1) Action: This enzyme hydrolyzes the α-1,6-glucosidic linkages of pullulan and mainly forms maltotriose.

Figure 2:
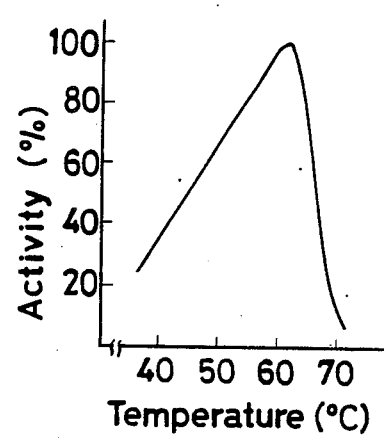
FIG. 2 is a graph showing the optimum temperature examined using pullulan as the substrate.

(2) Operating temperature range and optimum operating temperature: This enzyme has been found to show its activity at temperatures up to about 80° C. and possess its optimum temperature in the range of 60° to 63° C. (withstanding 30 minutes' reaction in the presence of 1% of pullulan and 0.05M tris buffer (pH 7.0) (FIG. 2).

Figure 1:
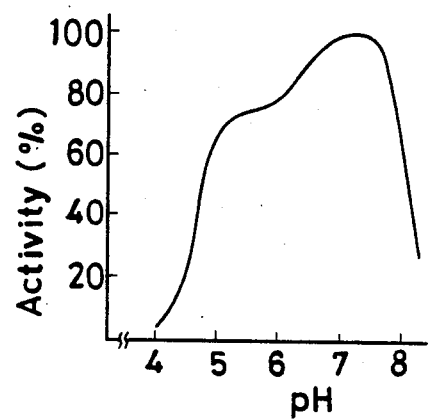
FIG. 1 is a graph showing the optimum pH examined using pullulan as the substrate.

(3) Operating pH range and optimum pH: This enzyme has been found to show its activity in a wide pH range of about 4 to about 10 and, in view of fIG. 1 showing peaks at about 5 and in the range of 7 to 7.5, possess its optimum pH in a wide range of about 5 to about 7.5 (withstanding 30 minutes' reaction at 55° C. in the presence of citric acid-$Na_2HPO_4$ buffer, phosphate buffer and 2% of pullulan).

(4) Thermal stability: In an experiment which involved maintaining this enzyme in the presence of 0.05M tris buffer (pH 7.0) at 50° C., 55° C. and 60° C. for ten minutes and then testing the mixture for residual activity with pullulan as a substrate, the enzyme was found to suffer from virtually no loss of activity after ten minutes' heating at 50° C., loss of about 30% of activity afterten minutes' heating at 55° C. and loss of about 80% of activity after ten minutes' heating at 60° C.

(5) pH stability: The enzyme has been found to retain stability at a pH value in the range of about 5 to about 10 by an experiment involving the steps of allowing the enzyme to stand at 30° C. for three hours in the presence of 0.1M acetate or phosphate buffer and testing for residual activity with pullulan as a substrate.

(6) Inhibitor: This enzyme undergoes not less than 90% of inhibition by each of $HgCl_2$ and $AgNO_3$ used in a concentration of $1 \times 10^{-3}$M and about 70% of inhibition by $ZnSO_4$ used in the same concentration.

(7) Stabilizer: This enzyme exhibits considerably increased thermal stability in the presence of calcium ion and, when reacted with 1% of pullulan for 30 minutes, is found to possess its optimum temperature of about 65° C. in the presence of calcium chloride used in a concentration of $1 \times 10^{-2}$M.

(8) procedure for purification: This enzyme can be obtained by adsorbing the enzyme from the filtrate of the liquid fermentation broth on calcium phosphate gel, washing the gel with distrilled water and extracting the enzyme with 0.5M KCl or $KH_2PO_4$, and purified to the chromatographic, electrophoretic and ultracentrifugal homogeneity by DEAE-Sepharose column chromatography, column chromatography using Biogel (A-1.5 m) and re-chromatography using the same column.

(9) Molecular weight: The molecular weight of this enzyme as determined by Biogel (A-0.5 m) is about 550,000.

(10) Procedure for determination of activity: This enzyme is added in a suitable amount to 0.5 ml of a 1% pullulan solution (pH 7.0) obtained by dissolving pullulan in 0.1M phosphate buffer. The mixture is made up to a total volume of 1 ml with water and incubated at 40° C. The amount of this enzyme which is required in producing reducing power equivalent to $1\mu$ mole of glucose after one minute standing under the aforementioned conditions is defined as one unit.

As described above, the pullulanase activity is found to possess an extremely wide optimum pH range of about 5 to about 7.5 and an optimum temperatuire range of 60° to 63° C. This is a highly thermostable enzyme. It is, therefore, proper to conclude that this is a novel pullulanase-like enzyme different from the pullulanese-like enzyme different from the pullulanases originating in microorganisms of genus Bacillus heretofore known to the art such as, for example, disclosed in Agric. Biol. Chem., 40, 1523 (1976) (optimum pH 6 to 6.5 and optimum temperature 50° C.), Japanese Patent Publication SHO 59(1984)-39630 (optimum pH 7.0 and optimum temperature 45° C.), and Japanese Patent Public Disclosure SHO 57(1982)-174089 (optimum pH 3.5 to 5.5 and optimum temperature about 60° C.).

The aforementioned pullulanase-like enzyme is produced by a bacterium isolated from soil and identified to be Bacillus subtilis (FERM BP-672). After various studies conducted for improving this microorganism in its ability to produce the enzyme, the inventor has found a strain possessed of an enhanced ability to produce the pullulanese-like enzyme among the mutants resistant to Tunicamycin induced by exposure to ultraviolet light or chemical treatment with nitrosoguanidine. This strain grows fairly well on a culture medium containing Tunicamycin (25–100 μg/ml), whereas its parent strain fails to show any growth. Thus, this strain is considered to be a novel variant of Bacillus subtilis in the sense that it shows resistance to Tunicamycin and possesses a notably high ability to produce the pullulanase-like enzyme. It has been designated as Bacillus subtilis TU strain, deposited with Fermentation Research Institute, Agency of Industrial Science & Technology on Oct. 13, 1984 under FERM 7893, and also transferred to the International Deposition based on the Budapest Treaty on Dec. 20, 1984 and designated FERM BP-684.

Table 1 shows typical abilities of the parent strain (FERM BP-672) of Bacillus subtilis and the Bacillus subtilis TU strain (FERM BP-684) in the production of the pullulanase-like enzyme of this invention.

TABLE 1

| Microorganism | Amount of enzyme produced (unit/ml of medium) |
| --- | --- |
| Parent strain | 0.38 |
| Bacillus subtilis TU strain | 11.8 |

It is noted from this table that the ability of the Tunicamycin-resistant mutant TU strain to produce the pullulanase-like enzyme is conspicuously high as compared with the same ability exhibited by the parent strain.

The mycological properties of the Bacillus subtilis and Bacillus subtilis TU strain will be shown below. The mycological properties of the parent strain are not shown since they are substantially the same as those of *Bacillus subtilis* TU strain.

(1) Morphological property: Rod in shape, 0.5 to 0.7μ×0.8 to 1.2μ in size, non-motile, gram positive, spores spherical or ellipsoidal.

(2) Characteristics of culture:
  (a) Nutrient agar slant culture—Smooth surface, good growth, light yellow in the latter part of the culture.
  (b) Glucose-nutrient agar slant culture—Growth inferior to that in the nutrient agar slant culture.
  (c) Nutrient broth culture—Growth not good, turbidity produced, sedimented.
  (d) Citrate agar slant culture—Growth scant.
  (e) Pepton-gelatin stab culture—Slowly liquefied.
  (f) Milk culture—Casein coagulated and peptonized.
  (g) Potato culture—Growth not too good.

(3) Biochemical property:
  (a) Reduction of nitrate—Negative.
  (b) Catalase—Positive.
  (c) Tyrosinase—Negative.
  (d) Indol—Not produced.
  (e) Utility of citric acid—Positive.
  (f) Formation of hydrogen sulfide—Positive.
  (g) Urease—Negative.
  (h) Hydrolysis of starch—Positive.
  (i) Utility of carbohydrate—Acids produced but no gas produced from carbohydrates, such as D-glucose, D-fructose, D-mannose, D-galactose, sucrose, maltose, lactose, starch, dextrin, glycogen, D-xylose, arabinose and L-arabinose.

(4) pH and temperature for growth: This bacterium shows better growth on the alkaline pH side of 7.5 to 8.5 than in the neighborhood of a neutral pH, its optimum growth at 35° to 45° C. and its best growth at about 50° C.

The pullulanase-like enzyme of the present invention possesses the α-amylase activity which hydrolyzes the α-1,4-glucosidic linkages present as in amylose, amylopectin, and glycogen and forms maltose and maltotriose in addition to the activity to hydrolyze the α-1,6-glucosidic linkages and effect hydrolysis of pullulan into maltotriose. Compared with pullulanases and isoamylases which are destitute of the α-amylase activities, therefore, the pullulanase-like enzyme, when used in conjunction with glucoamylase for saccharification of starch, promotes the saccharification reaction of starch and enables the eventual yield of glucose to be increased by 0.5 to 3%. When glucoamylase alone is allowed to react upon liquefied starch of a concentration of 30%, for example, the yield is about 94 to 95%. When this glucoamylase is used in combination with a commercially available pullulanase, the yield of glucose is about 96.5%. When the pullulanase-like activity of this invention possessing the pullulanase activity of the same level is used in place of the ordinary pullulanase, glucose is obtained in a yield of 97.0 to 97.5%. Besides permitting such enhancement in the yield of glucose, the enzyme of the present invention notably shortens the time required for reaching the maximum saccharification ratio. This fact implies that the necessary amount of glucoamylase can be reduced.

When the enzyme of the present invention is made to act upon amylose, amylopectin, starch, glycogen, etc., it preponderantly forms maltose and maltotriose. Since this enzyme possesses the ability to cleave the α-1,6-glucosidic linkages, it enables maltose and maltotriose to be formed in extremely high yields. When this enzyme is allowed to act on liquefied starch, for example, the maltose and maltotriose are obtained each in a concentration of about 40 to 50%. None of the amylases heretofore known to the art is capable of producing maltose and maltotriose in such a sugar composition as described above. The saccharide which is obtained by using the enzyme of this invention combines the properties of maltose and maltotriose and, therefore, is utilizable as a food additive serving variously as a sweetening agent, sweet taste adjuster, or food extender. The enzyme to be used in this invention is excellent in thermal stability. Even at the optimum working and critical temperature of 60° C. for glucoamylase, the enzyme can continue its reaction for a long time. Moreover, it can be advantageously utilized within the desirable optimum pH range of 4.5 to 5.0 for glucoamylase.

When the enzyme of this invention is adopted in the saccharification of starch, therefore, it brings about various effects.

The production of the pullulanase-like enzyme of the present invention is accomplished by culturing the strain of *Bacillus subtilis* on a culture medium containing nitrogen sources, carbon sources, etc. Examples of the nitrogen sources include organic nitrogen sources such as pepton, meat extract, yeast extract, casein, corn steep liquor, soybean meal, fish meal etc., and inorganic nitrogen sources including ammonium salts such as ammonium chloride, ammonium nitrate, ammonium phosphate etc., nitrates such as sodium nitrate and potassium nitrate, urea etc.

As carbon sources, generally starch, dextrin, maltose, or glucose are used. As nutritional materials for making up for such nitrogen and carbon sources, phosphates, magnesium salts, and small amounts of manganese and iron compounds are added.

Although the culture can be carried out at a pH value of about 5 to about 9 at a temperature in the range of 25° to 55° C., it is generally performed aerobically at pH 7-9 and 30° C. for two to four days. The enzyme is substantially produced extracellularly. After the culture, therefore, the broth is filtered or centrifuged to remove the cells. The supernatant is recovered. The supernatant so recovered is concentrated when necessary and treated with ammonium sulfate or sodium nitrate to salt out the enzyme or mixed with acetone, isopropanol, ethanol, methanol, or some other suitable organic solvent to separate the enzyme in the form of precipitate. The enzyme is recovered in the form of a concentrated solution or dry solid.

The saccharification of starch by the use of the enzyme of this invention either in its independent form or in combination with glucoamylase or β-amylase is carried out generally at pH 4-9 and 40° to 70° C.

Now, the present invention will be described more specifically below with reference to working examples. This invention is not limited by these examples.

EXAMPLE 1

A strain of *Bacillus subtilis* (FERM BP-672) was suspended in distilled water and irradiated with the ultraviolet light (15 W) from its source at a distance of about 30 cm for 5 minutes. Part of the irradiated suspension was placed in a culture medium containing 75 μg of Tunicamycin per ml (containing 1% of polypepton, 1% of soluble starch, 0.3% of $K_2HPO_4$, and 0.1% of $MgSO_4.7H_2O$) and aerobically cultured therein at 30° C. for three days. The grown microorganism was sprayed on a plate culture medium with the same culture medium containing agar and incubated at 30° C. The colonies which grew were preserved on a slant medium of the same composition. In the Tunicamycin-resistant mutants so produced, there was obtained in high frequency a strain of enhanced activity to produce the pullulanase-like enzyme. *Bacillus subtilis* TU strain (FERM BP-684) was thus obtained.

In Erlenmeyer flasks having an inner volume of 200 ml, 10 ml of a culture medium (pH 7.0) containing 5% of soybean meal, 0.6% of corn steep liquor, 0.3% of meat extract, 0.3% of potassium phosphate, 0.1% of magnesium sulfate, 2% of soluble starch, 0.5% of urea, 0.06% of sodium n-dodecyl benzene sulfornate, $5 \times 10^{-5}$M of copper sulfate, $2.5 \times 10^{-6}$M of manganese chloride, $1 \times 10^{-3}$M of calcium chloride, $1 \times 10^{-4}$M of zinc sulfate, and $1 \times 10^{-5}$M of iron sulfate was sterilized at 120° C. for 20 minutes. Then, a *Bacillus subtilis* TU strain (FERM BP-684) thus obtained and a parent strain (FERM BP-672) were inoculated to the culture medium in the separate flasks and shaken cultured (160 rpm) at 30° C. for four days. After the culture, the broths were centrifuged. The supernatants consequently obtained were tested for pullulanese activity. The results are shown in Table 2.

TABLE 2

| Microorganism | Pullulanase activity (unit/ml of medium) |
|---|---|
| Parent strain | 0.35 |
| TU strain | 16.7 |

EXAMPLE 2

In an Erlenmeyer flask having an inner volume of 200 ml, 30 ml of a culture medium (pH 7.2) containing 5% of soybean meal, 0.5% of corn steep liquor, 0.4% of meat extract, 0.3% of K$_2$PO$_4$, 0.1% of MgSO$_4$.7H$_2$O, 2% of soluble starch, 0.5% of urea, 0.1% of sodium n-dodecyl benzene sulfonate, $5 \times 10^{-5}$M of CuSo$_4$, $2.5 \times 10^{-6}$M of MnCl$_2$, $1 \times 10^{-3}$M of CaCl$_2$, $1 \times 10^{-4}$M of ZnSO$_4$ and $1 \times 10^{-5}$M of FeSO$_4$ was sterilized by the conventional method and, with a strain of *Bacillus subtilis* TU (FERM BP-684) inoculated thereto, subjected to shaken culture at 30° C. for three days. At the end of the culture, the culture broth was centrifuged to remove cells and obtain the supernatant. The supernatant was tested for the pullulanase activity and α-amylase activity. Consequently, the pullulanase activity and α-amylase activity were found to be 9.6 units and 45.2 units respectively per ml of the culture medium.

The α-amylase activity was determined by the following procedure.

The enzyme was added in a suitable amount to 0.5 ml of 1% soluble starch solution (pH 7.0) obtained by dissolving soluble starch in 0.1M phosphate buffer. The mixture was made up to a total volume of 1 ml with water and inoculated at 40° C. The amount of this enzyme which was required in producing reducing power equivalent to 1μ mol of glucose after one minute standing under the aforementioned conditions was defined as one unit.

EXAMPLE 3

To 250 ml of the supernatant of a strain of *Bacillus subtilis* TU (FERM BP-684) cultured in a culture medium having the same composition as that of the culture medium used in Examle 2 was added dropwise 150 ml of 0.4M Na$_2$HPO$_4$ and 150 ml of 0.4M CaCl$_2$ to obtain calcium phosphate gel and, at the same time, an enzyme was adsorbed on the gel. Then, the resultant gel was filtrated by a glass filter to recover the adsorbed substance. The recovered substance was sufficiently washed with distilled water and treated with 200 ml of 0.5M K$_2$HPO$_4$ to elute the enzyme. The eluted enzyme was dialyzed and concentrated.

Figure 3:
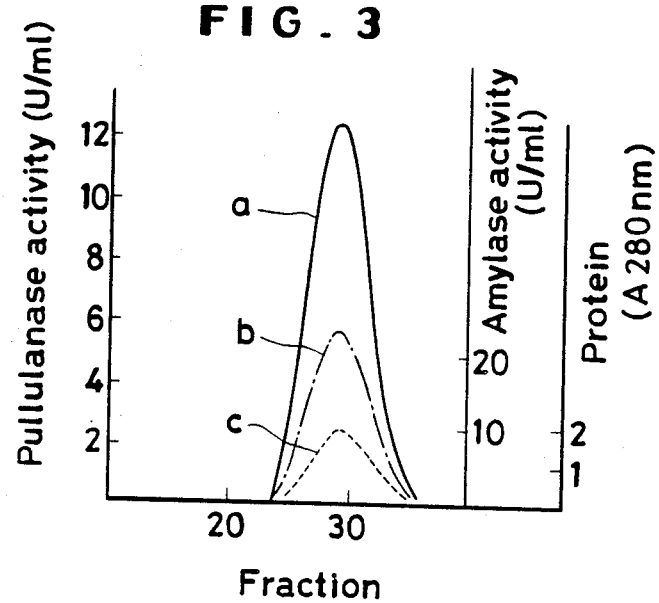
FIG. 3 is a graph showing pullulanase activity, amylase activity, and protein elusion patterns (absorption at 280 nm) as determined by the use of a column packed with Biogel A-1.5 m.

Subsequently, the resultant enzyme was purified with the DEAE-Sepharose column equilibrated with $2.5 \times 10^{-3}$M tris buffer (pH 7.0). Pullulanase eluted with the same buffer was collected, concentrated and dialyzed and thereafter applied to Biogel A-1.5 m column equilibrated with $2.5 \times 10^{-3}$M tris buffer (pH 7.0). A fraction having pullulanase activity was collected. The collected pullulanase was repeatedly subjected to re-chromatography in the same column. FIG. 3 shows elution pattern curves obtained by the use of Biogel A-1.5 m column(1.5×87 cm). It is noted from FIG. 3 that the enzyme thus purified exhibits protein curve "c", pullulanase activity curve "a" and α-amylase activity curve "b" whose elution patterns coincide with one another in terms of the fraction. The enzyme finally recovered was found to have 585 units of pullulanase activity and 1070 units of amylase activity.

EXAMPLE 4

In an Erlenmeyer flask having an inner volume of 200 ml, 30 ml of a culture medium (pH 7.2) containing 5% of sardine meal, 0.4% of corn steep liquor, 0.3% of K$_2$HPO$_4$, 0.1% of MgSO$_4$.7H$_2$O, 2% of soluble starch, 1% of urea, 0.06% of sodium n-dodecyl benzene sulfonate, $5 \times 10^{-5}$M of CuSO$_4$, $2.5 \times 10^{-6}$M of MnCl$_2$, $1 \times 10^{-3}$M of CaCl$_2$, $1 \times 10^{-4}$M of ZnSO$_4$ and $1 \times 10^{-5}$M of FeSO$_4$ was sterilized by the conventional method and, with a strain of *Bacillus subtilis* TU (FERM BP-684) inoculated thereto, subjected to shaken culture at 30° C. for three days. At the end of the culture, the culture broth was centrifuged to remove cells and obtain the supernatant. The supernatant was tested for the pullulanase activity. Consequently, the pullulanase activity was found to be 6.9 units per ml of the culture medium.

EXAMPLE 5

The enzyme prepared in Example 3 was used together with commercially available glucoamylase in starch saccharification reaction.

Potato starch (DE 7.7) liquefied with commercially available liquefying enzyme (α-amylase) was used. (Both the glucoamylase and the liquefying enzyme can be obtained from Amano Pharmaceutical Co., Ltd., Japan and Nove Japan Co., Ltd.) Liquefied starch having a solid content of 3 g, 0.2% of glucoamylase (an enzyme for industrial use produced by Nove Japan Co., Ltd.) based on the solid content of the liquefied starch was used as specimen "A". To the specimen "A" the same glucoamylase of the same amount and commercially available pullulanase and the same glucoamylase of the same amount and the pullulanase-like enzyme of the present invention prepared in Example 3 were respectively added to obtain specimens "B" and "C". (Commercially available pullulanase and the pullulanase-like enzyme of this invention were measured by the same activity determination procedure as mentioned hereinbefore except for use of acetate buffer in place of the phsophate buffer, measurement pH of 5.0, and each enzyme was added at 0.5 unit per gram of the substrate.)

The three resultant specimens were subjected to saccharification reaction at 57.5° C. at pH 4.8 to 5.0 in the presence of $1 \times 10^{-2}$M CaCl$_2$. The results obtained were as shown in Table 3 and Table 4.

TABLE 3

| Sacchari-fication Time (hour) | Dextrose Equivalent | | |
|---|---|---|---|
| | Specimen A (control) | Specimen B (comparison) | Specimen C (present invention) |
| 1 | 51.2 | 56.9 | 57.9 |
| 2 | 69.9 | 71.4 | 74.6 |
| 3 | 78.5 | 81.1 | 83.0 |
| 5 | 89.0 | 92.3 | 92.5 |
| 20 | 94.3 | 95.3 | 96.9 |

TABLE 4

| Sacchari-fication Time (hour) | Yield of Glucose (%) | | |
|---|---|---|---|
| | Specimen A (control) | Specimen B (comparison) | Specimen C (present invention) |
| 22 | 82.9 | 93.8 | 94.2 |
| 25 | 95.0 | 95.6 | 97.1 |
| 28 | 95.0 | 95.5 | 96.0 |

Table 3 shows the dextrose eqivalents (the amount of reducing sugar in total sugar was determined as glucose) obtained at one, two, three, five and 20 hours after the start of the saccharification reaction. Total sugar was determined by the phenol-sulfate method and the reducing sugar by the potassium ferricyanide method. It is clearly noted from Table 3 that the speciment "C" using the enzyme of the present invention exhibited promoted saccharification at the initial time of the saccharification reaction.

Table 4 shows the glucose content in the saccharized materials determined by high speed liquid chromatography method. It is clearly noted from Table 4 that the specimen "C" using the pullulanase-like enzyme of the present invention exhibited the maximum yield of glucose of 97.1% and that the saccharification reaction of the specimen "C" was considerably promoted in view of the yield of glucose after a saccharification reaction of 22 hours in comparison with those of the specimens "A" and "B".

EXAMPLE 6

Similarly to Example 5, saccharification reactin was carried out by the addition of the enzyme of the present invention in an amount of 0.5 unit per gram of the substrate at 55° C. at pH of 4.5 to 5.3. After 24 hours from the start of the saccharification reaction, yields of glucose produced were measured every two hours by high speed liquid chromatography. The results obtained are as shown in Table 5 which shows the maximum yield of glucose at each of the saccharification pH values.

TABLE 5

| | pH | Yield of Glucose (%) |
|---|---|---|
| Specimen A | About 4.5 | 95.0 |
| Specimen C | About 4.5 | 96.6 |
| Specimen C | About 4.7 | 96.8 |
| Specimen C | About 5.1 | 97.1 |

It is clearly noted from Table 5 that the specimen "C" using the enzyme of the present invention functioned effectively at pH in the range of 4.5 to 5 which is the optimum pH for glucoamylase and could increase the yield of glucose by about 2% in comparison with that in the case of the specimen "A" as the control (the liquefied starch having glucoamylase only).

EXAMPLE 7

Similarly to Example 5, saccharification reaction was carried out at 55° C. at pH of about 5, with the amount of the enzyme varied to 0.2, 0.5 and 0.75 unit per gram of the substrate. The results obtained are as shown in Table 6.

TABLE 6

| Amount of Enzyme Used (unit/g) | Yield of Glucose (%) | | |
|---|---|---|---|
| | 23 hours | 26 hours | 42 hours |
| 0 | 91.9 | 93.2 | 94.3 |
| 0.2 | 95.1 | 95.3 | 96.8 |
| 0.5 | 96.8 | 97.0 | 97.1 |
| 0.75 | 97.4 | 97.3 | 96.9 |

EXAMPLE 8

In view of the fact that the enzyme of the present invention can be firmly adsorbed on calcium phosphate gel, the enzyme adsorbed and immobilized on calcium phosphate gel was used.

To be specific, calcium phosphate gel was prepared by equivalently mixing 0.5M Na$_2$PO$_4$ and 0.5M CaCl$_2$ and the enzyme of the present invention was immobilized on the prepared calcium phosphate gel. The gel having the enzyme at 1.2 unit per ml of gel suspension was used.

The enzyme immobilized on the calcium phosphate gel (one unit per gram of the substrate) was added to the mixture containing the liquefied starch used in Example 5 and glucoamylase to obtain a specimen "D". Saccharification reaction of the specimen "D" was carried out under slight shaking at 55° C. at pH of about 5. The resultant specimen was repeatedly subjected to centrifugal separation to recover the immobilized enzyme every 24 hours with the liquefied starch replaced by a new one and with the recovered immobilized enzyme used repeatedly. The results obtained are as shown in Table 7.

TABLE 7

| Number of Times Immobilized Enzyme was used | Yield of Glucose (%) | |
|---|---|---|
| | Specimen A (control) | Specimen D (present invention) |
| 1 | 94.4 | 96.7 |
| 2 | 94.4 | 96.2 |
| 3 | 94.4 | 96.1 |
| 4 | 94.4 | 96.0 |
| 5 | 94.4 | 95.9 |

It is clearly noted from Table 7 that the yield of glucose by the use of the immobilized enzyme was about 96% which is lower by about 0.5 to 1% than that by the use of a free enzyme but is higher by about 1.5 to 2% than in the case of non-use of the enzyme.

EXAMPLE 9

The enzyme (having pullulanase activity of one unit) prepared in Example 3 was added to 1 g of DE 4.2 of liquefied starch. The mixture was made up to a total volume of 10 ml and reacted at 50° C. for two days, with the pH maintained in the neighborhood of 7. After the reaction, the sugar composition of saccharized material was analyzed by high speed liquid chromatography. The results obtained are as shown in Table 8.

TABLE 8

| Sugar Composition | Content (%) |
| --- | --- |
| Glucose | 1.4 |
| Maltose | 41.2 |
| Maltotriose | 41.0 |
| Maltotetraose | 4.5 |
| Others | 11.9 |

It is clearly noted from Table 8 that the saccharized material obtained was composed preponderantly of maltose and maltotriose, which each accounted for about 40% of the total material.

EXAMPLE 10

The culture broth (having pullulanase activity of 0.5 unit) of the strain of *Bacillus subtilis* TU (FERM BP-684) obtained in Example 2 was added to 1 g of soluble starch. The mixture was made up to a total volume of 10 ml with water and reacted at 50° C. at pH of 7 for two days. After the reaction, the sugar composition of the saccharized material was analyzed by high speed liquid chromatography. The results obtained are as shown in Table 9.

TABLE 9

| Sugar Composition | Content (%) |
| --- | --- |
| Glucose | 4.6 |
| Maltose | 37.2 |
| Maltotriose | 53.7 |
| Others | 4.5 |

EXAMPLE 11

500 units of commercially available plant β-amylase was added to 2 g of liquefied starch (DE 4.2). The mixture was made up to a total volume of 10 ml with water and reacted at 55° C. for 20 hours. The saccharized material thus obtained was composed of 1.1% of glucose, 52.5% of maltose, 4.9% of maltotriose and 41.5% of others.

The enzyme (having pullulanase activity of one unit) prepared in Example 2 was added to part of the aforementioned saccharized material (having a solid content of 1 g). The resultant mixture was reacted at 50° C. for 24 hours. The saccharized material thus obtained was found to have a composition of 4.6% of glucose, 60.5% of maltose, 30.9% of maltotriose and 4.0% of others.

What is claimed is:

1. A method for the production of a pullulanase-like enzyme possessing an α-amylase activity, comprising the steps of culturing a strain of genus *Bacillus subtilis* (FERM BP-672) on a derviative thereof capable of producing a pullulanase-like enzyme possessing an α-amylase activity to hydrolyze starch chiefly into maltose and maltotriose and collecting said enzyme from the culture broth.

2. A method according to claim 1, wherein said derivative is a *Bacillus subtilis* strain resistant to Tunicamycin.

3. A method according to claim 2, wherein said Tunicamycin-resistant strain is *Bacillus subtilis* TU strain (FERM BP-684).

* * * * *

UNITED STATES PATENT AND TRADEMARK OFFICE
CERTIFICATE OF CORRECTION

PATENT NO. : 4,657,865
DATED : April 14, 1987
INVENTOR(S) : TAKASAKI, Yoshiyuki

It is certified that error appears in the above-identified patent and that said Letters Patent is hereby corrected as shown below:

On the Title Page:
THE NUMBER OF DRAWINGS WAS RECORDED INCORRECTLY IN THE LETTERS PATENT.

SHOULD READ:

3 DRAWING FIGURES

Signed and Sealed this

Eleventh Day of August, 1987

Attest:

DONALD J. QUIGG

*Attesting Officer*     *Commissioner of Patents and Trademarks*